United States Patent

Mini et al.

[11] Patent Number: 5,157,894
[45] Date of Patent: Oct. 27, 1992

[54] ORIENTATION AND LOADING DEVICE FOR VIALS IN GENERAL AND SYRINGE VIALS IN PARTICULAR

[75] Inventors: Claudio Mini, Tavazzano; Rodolfo Scacco, Limbiate, both of Italy

[73] Assignee: Italfarmaco S.p.A., Milan, Italy

[21] Appl. No.: 720,474

[22] PCT Filed: Dec. 5, 1990

[86] PCT No.: PCT/EP90/02103
§ 371 Date: Jun. 25, 1991
§ 102(e) Date: Jun. 25, 1991

[87] PCT Pub. No.: WO91/06475
PCT Pub. Date: May 16, 1991

[30] Foreign Application Priority Data

Dec. 14, 1989 [IT] Italy ................. 22693 A/89

[51] Int. Cl.$^5$ ................. B65B 23/22; B65B 19/34; B65B 21/06; B65B 5/08
[52] U.S. Cl. ................. 53/148; 53/154; 53/539; 53/236; 53/246
[58] Field of Search ......... 53/148, 154, 539, 236, 53/246, 251; 198/477.1, 575, 576, 803.01, 860.1

[56] References Cited

U.S. PATENT DOCUMENTS

| 3,027,699 | 4/1962 | Miller et al. | 53/251 X |
| 3,133,393 | 5/1964 | Jones | 53/246 X |
| 3,946,536 | 3/1976 | Serra | 53/251 X |
| 4,233,799 | 11/1980 | Caille | 53/246 X |
| 4,627,215 | 12/1986 | Walz | 53/246 |
| 4,982,556 | 1/1991 | Tisma | 53/251 X |

FOREIGN PATENT DOCUMENTS

| 0018611 | 11/1980 | European Pat. Off. |
| 0134629 | 3/1985 | European Pat. Off. |
| 0320367 | 6/1989 | European Pat. Off. |
| 2479142 | 10/1981 | France |

Primary Examiner—Horace M. Culver
Attorney, Agent, or Firm—Ladas & Parry

[57] ABSTRACT

An orientation and loading device for vials, and in particular syringe vials (A), which are disposed with their axis substantially vertical. The vials are fed by a feeder (1) to an endless conveyor (5) comprising a plurality of orientable cells (6), each of which removably receives a fed vial. In an assigned position (R) of the conveyor (5) the cells (6) and hence the vials received therein lie substantially horizontal above a container (7) provided with several cavities (8) for receiving the vials and intended to form part of the package in which the vials are sold. When in this horizontal position, a release means (9) operates to release the vials (A) from the cells (6) and cause them to fall into the underlying container (7), for example a thermoformed container.

7 Claims, 2 Drawing Sheets

ORIENTATION AND LOADING DEVICE FOR VIALS IN GENERAL AND SYRINGE VIALS IN PARTICULAR

TECHNICAL FIELD

This invention relates to a device for firstly orientating vials in general and syringe vials in particular, and then loading them into their sales packages, in particular into thermoformed containers, comprising a seat for each vial, and which are then themselves boxed.

BACKGROUND ART

With particular but not exclusive reference to syringe vials it is known that one of the problems not yet satisfactorily solved is that of loading syringe vials into thermoformed tray containers with industrially required speed, with precision and without causing breakage or damage, these containers when closed and boxed representing the method by which the medicament contained in the syringe vials is sold. Their intrinsic fragility facilitates damage to the vials and to syringe vials in particular, this being difficult to reconcile with the required industrial speed, which itself detracts from adequate precision.

In this respect to load the syringe vials they must firstly be orientated from their vertical position to a horizontal position, and when in this position they must be fed into an underlying recessed container in such a manner that each syringe vial is exactly received by a separate cavity in the container, such cavities being only slightly larger than the syringe vial to be held, for reasons of compactness and adequate retention.

DISCLOSURE OF INVENTION

The traditional methods employed for this purpose are unsatisfactory for one reason or another, the main object of the present invention therefore being to provide a device which is able to totally satisfy the requirements of speed, precision and vial intactness during the said operations. This and further objects which will be more apparent from the detailed description given hereinafter are attained by a device characterised essentially by comprising: a feed section, an endless conveyor with orientatable cells, each for removably receiving at least one vial fed to it by the feed section, and means for modifying the orientation of the cell and hence of the vial during the movement of the conveyor from the feed section to a discharge section which comprises means for simultaneously releasing a predetermined number of vials from the relative cells, with their consequent fall into an underlying container.

In this text the term "vial" also and in particular includes syringe vials (as already implicitly stated).

BRIEF DESCRIPTION OF DRAWINGS

A preferred embodiment of the invention is illustrated on the accompanying drawing in which.

BEST MODE OF CARRYING OUT THE INVENTION

Figure 1:
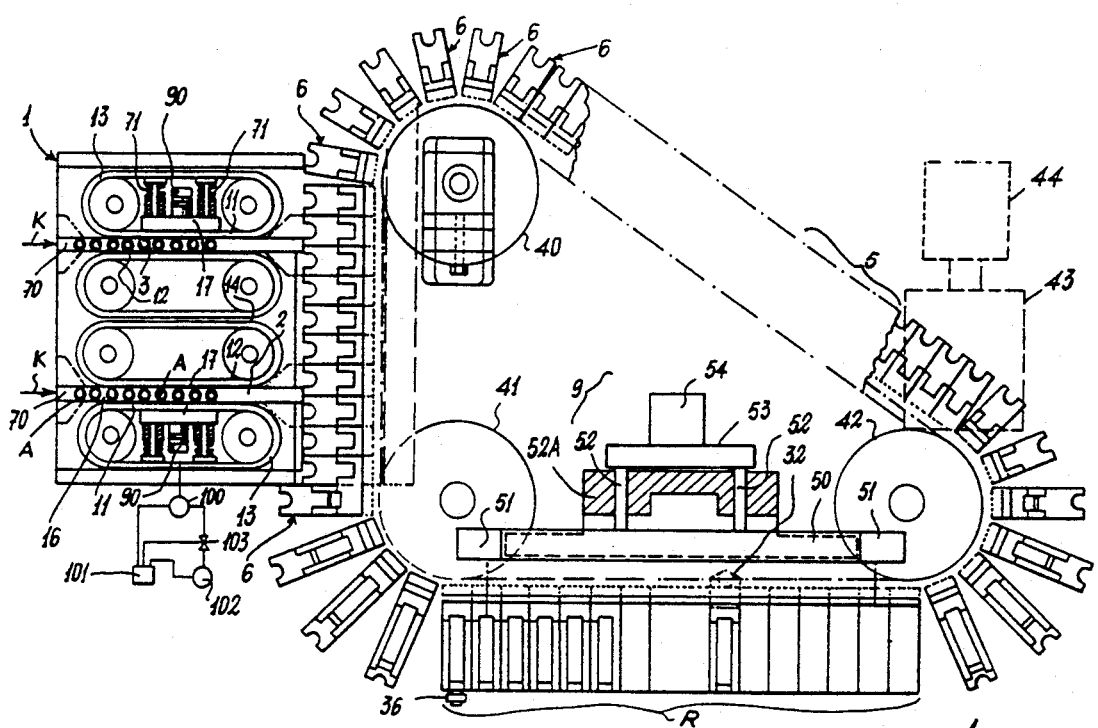
FIG. 1 is a schematic plan view of the device of the invention.

In the figure the reference numeral 1 indicates overall a feed section which feeds the vials A with vertical orientation along two parallel lines 2, 3 to an endless conveyor indicated overall by 5, and specifically into orientatable cells 6 with which the conveyor in question is formed. During the movement of the conveyor the cells change their orientation so as to move the vials A from the vertical position in which they are received in the cells, to a horizontal position.

Within that rectilinear portion of the conveyor 5 along which the cells 6 are horizontally orientated, means 9 are operated to simultaneously release a determines number of horizontal vials from the relative cells so that they arrive by gravity into an underlying container 7 divided into cavities 8, each designed to hold one vial. In detail, the feed section 1 comprises two parallel feed lines 2, 3. Each of these lines is bounded by active confronting portions 11, 12 of a pair of endless belts or bands 13, 14 situated at such a distance apart as not to exert any conveying action on the vials A which via their flange A1 rest on a pair of support parallel bars 15, 16 positioned at a height greater than that of the belts 13, 14. On the inner side of the active portions 11, 12 of the belts there is provided a presser 17 operated by for example an hydraulic, a pneumatic or electromagnetic actuator 90 against the action of spring 71.

More particularly, in this example, each presser formed by a metal plate is connected with two parallel guide rods 72 axially slidable in fixed guides 73 and provided with an head 74 at their free ends. A spring 71 is mounted between head and guide.

The actuator 90 located between the guide rods comprises a cylinder wherein a piston connected with the presser is located. The cylinder of each actuator is hydraulically connected with an electromagnetic three-way valve 100.

In its unenergized status the valve maintains the connection between the cylinder and a liquid reservoir 101 and in its energized status it closes said connection and connects the cylinder with a pump 102 which intakes from the reservoir 101. A valve 103 will exhaust the delivery of the pump to the reservoir 101 when the connection between pump and actuator is closed.

When the actuator 90 is activated (pulsewise for a short time) the presser acts on the active portion 11, 12 in front of it, and which is thus urged against the vials A, which are located along the line 2, 3 and applied also against the other belt; this causes a rapid motion to be transmitted to the vials in the direction of the arrow K, i.e. towards the conveyor 5 comprising orientatable cells 6, so that the first vial of the row enters a cell, which is in an aligned position to receive it.

The conveyor 5 comprises a plurality of identical orientatable cells 6. The cells 6 comprise a rear part 20 rigid with drive chains 21 and having a constant orientation, i.e. vertical. In the top and bottom of the rear part 20 there are provided grooves 22 into which stationary guide bars 23 penetrate to oppose the thrusts which are exerted on the cells 6 and which are explained hereinafter.

The effectively orientatable part 25 of the cell 6 is hinged to the lower end of the rear part 20 at 24. Said orientatable part 25 comprises a groove of rounded base 26, its axis being perpendicular to the direction of movement of the conveyor 5. As can be seen from FIG. 2 this groove receives the syringe A when it is fed by the feed section 1, as stated heretofore.

To enable the vial A to be thus received and subsequently adequately retained in the respective cell 6, the orientatable part 25 thereof is provided with a clamp 27 comprising a slot 28 and mounted on a pair of pins 29.

These pins are slidingly mounted against the action of a spring 30 in the orientatable part 25 and terminate in a common crosspiece 31 carrying an idle roller 32. A cam or guide 33, extending within the region in which the feed section 1 is provided and arranged to move the clamp 27 upwards, enables the vial A to enter the groove 26 with its flange A1 resting on the face 34 below the raised clamp 27, which is then lowered to lock the flange A1 and hence the vial A on leaving the vial loading region where said guide is provided.

On the same side as the clamp 27 but to the rear thereof the orientatable part 25 also comprises an appendix 35 carrying an idle roller 36, the axis of rotation of which is parallel to the axis of the groove 26. The purpose of this idle roller is to cooperate with fixed guides 40, 41 shown schematically on the drawing and distributed along the extension of the conveyor 5, their orientation and purpose being to control the orientation of the orientatable part 6 in such a manner that it passes gradually from vertical (FIG. 2) to horizontal (FIG. 3) at the point at which that section of the conveyor 5 within which the vials A are to be discharged from the relative cells and fall into the underlying container 7 begins.

Figure 2:
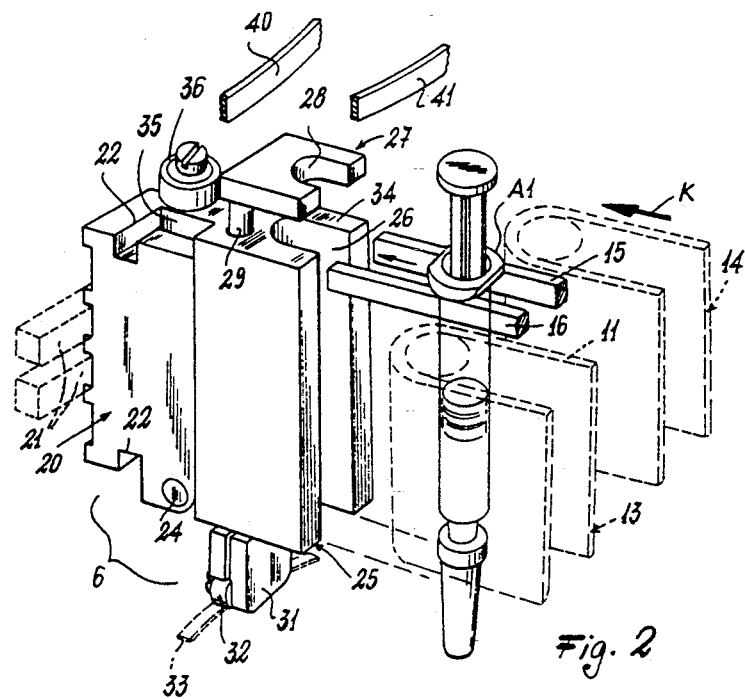
FIG. 2 is a perspective view of an orientatable cell, shown in the particular orientation which enables it to receive a vial.
Figure 3:
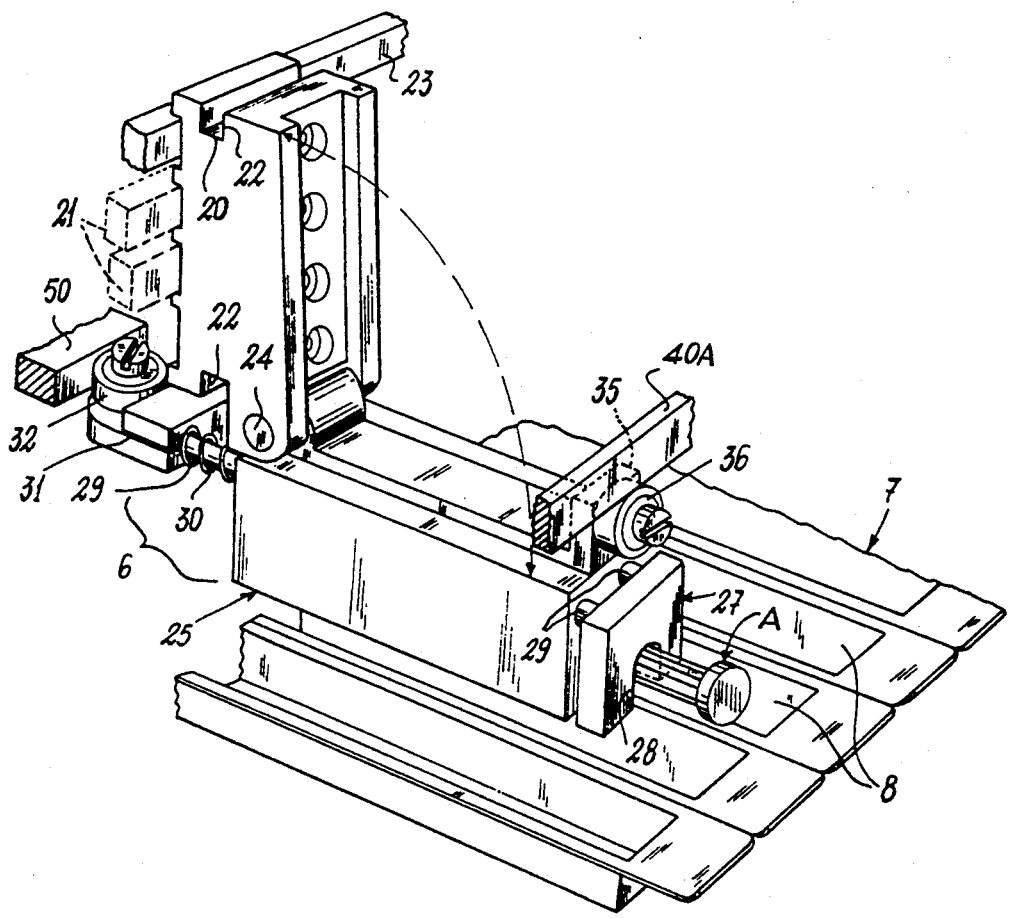
FIG. 3 is a perspective view of the orientatable cell, shown in the particular orientation which enable it to discharge the vial.

The orientation then returns to vertical at the exit from the discharge section R so that the cells again present themselves as in FIG. 2 before the feeding section 1, ready for receiving new vials.

The conveyor 5 moves along a substantially triangular path. At the respective vertices of the triangle there are provided idle deviation sprockets 40 (one for each chain 21) which are coaxial but are mounted conventionally to be able to adjust the tension of the chains 21, idle coaxial fixed-position sprockets 41, and coaxial drive sprockets 42 mounted at the exit of a reduction gear unit driven by an electric stepping motor 44.

At the discharge section R of the conveyor 5 and positioned to operate on several idle rollers 32 of the horizontally orientated cells 6 there is provided the discharge means 9, which comprises at least one thrust member 50 in the form of a crosspiece mounted slidingly in guides 51 in the direction of the arrows X (FIG. 1) and rigid with the ends of two rods 52 guided in a fixed support 52A and joined together by a second crosspiece 53 on which for example a double-acting electromagnetic or pneumatic actuator 54 acts.

A pulse provided by this actuator 54 moves the crosspiece 50 against the rollers 32 and these move the clamps 27 in the direction to release the flanges A1 of the vials A within the discharge section R, the vials then falling into the cavities 8 of the underlying container 7, such as a thermoformed container. To oppose the torque which the crosspiece 50 produces on the orientatable parts 25 of the cells, the guide 40 is extended to 40A (FIG. 3) within the discharge section R of the device so to counteract the torque.

Figure 4:
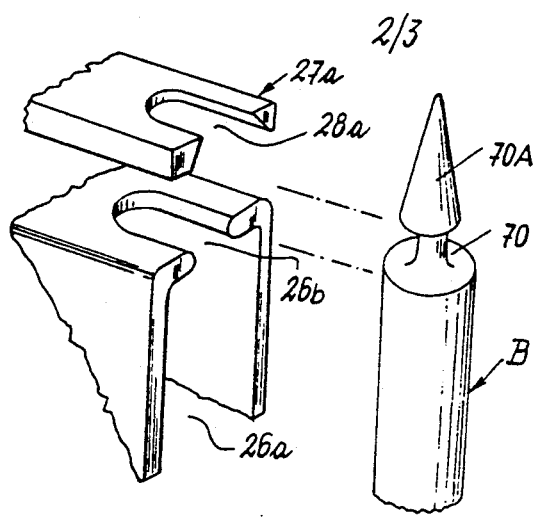
FIG. 4 is a partial perspective view of a detail of a differently shaped orientatable cell.

The device of the invention can be used with traditional vials and not only with the syringe vials shown. For such an application the cells or rather their orientatable part can have the shape shown in FIG. 4, in which the vial is indicated by 3, the groove 26a has a constriction at its top, at 26b, to support the vial at its constricted part 70, and the clamp 27a has an inclined-edge slot 28a to adapt to the conical shape of the end 80A of the vial B.

The operation is easily understood from the aforegoing description: the syringe vials A originating from any known upstream apparatus supplying them to the two lines 2, 3 (arrows K) of the feed section 1, are fed by this latter one by one (for each line) into the grooves 26 of the empty cells 6 as they gradually appear in front of these lines (see FIG. 2).

When such coincidence exists between the line and groove 26 (determined for example by proximity sensors or by processing the count of the steps undergone by the stepping motor which drives the conveyor 5), an hydraulic, electrical or pneumatic pulse is fed to the actuator 90 of the presser 17, which moves against the active portion (e.g. 11) of the belt (e.g. 13) which faces it, so that the vials are individually fed into the relative cells 6, the clamp 27 of which is raised (FIG. 2). The conveyor 5 conveys the loaded cells to the discharge region R, in which the vials A are positioned horizontally. When for example by processing the number of steps undergone by the stepping motor it is determined that a given number of loaded cells lie within the discharge region R, the device 9 is operated so that the appropriate clamps 27 open by the effect of the thrust exerted by the crosspiece 50, with the result that the corresponding vials fall into the underlying container 7, each into the corresponding cavity 8.

INDUSTRIAL APPLICABILITY

The device of the invention is applicable in the packaging industry.

We claim:

1. A device for orienting objects (A,B) and loading them into containers (7) provided with cavities (8) for containing said objects, said device comprising a feed station (1), an endless conveyor (5) with a plurality of orientable cells (6), said orientable cells each comprising a non-orientable support part (20) and an orientable support part (25) which is hinged to the non-orientable support part and which includes a seat (34) and a moveable clamp (27) for releasably retaining at least one object (A,B), the objects being fed to said cells at said feed station (1), means for moving said conveyor so that the cells are moved from said feed station (1) to a discharge station (R), means (38,40,41) for modifying the orientation of the orientable support parts of the cells as they pass to the discharge station (R) and means (32,50) for simultaneously releasing a predetermined number of objects (A,B) at the discharge station (R) by urging said movable support clamps (27) away from clamping engagement with said predetermined number of objects (A,B).

2. A device as claimed in claim 1, wherein the feed station (1) comprises at least one feed line (2,3) for feeding said objects (A,B), said at least one feed line being bounded by active portions (11,12) of a plurality of belts (13,14) and a controlled presser (17) at said active portions (11,12) for causing the objects (A,B) to be fed.

3. A device as claimed in claim 1 wherein the orientatable parts (25) of the cells (6) include rollers (36) and wherein said means for modifying the orientation of the orientable support parts includes stationary guides (40,41) which cooperate with the rollers (36) of the orientable support parts to effect rotary movement of said orientable support parts (25) with respect to said non-orientable support parts (20) as said stationary guides (40,41) engage said rollers causing said orientable support parts to change orientation as said conveyor moves.

4. Device as claimed in claim 1, wherein the seat (26) is provided by an elongated groove in each of said orientatable parts (25), said grooves being directed transversely to the direction of movement of the conveyor (5).

5. The device as claimed in claim 1, wherein said objects are syringes having flanges thereon, and wherein the seat (34) and the movable clamp (27) on each cell releasably engage the flanges of said syringes.

6. A device for orienting objects (A,B) then loading them into containers (7) provided with object cavities (8), said device comprising a feed station (1), an endless conveyor (5) with orientatable cells (6), each cell including means for removably retaining at least one object (A,B) fed to it by the feed station (1), means for moving such conveyor so that the cells are moved from the feed station (1) to a discharge station (R), means (38,40,41) for modifying the orientation of the cells (6) as they pass to the discharge section (R), means (32,50) for simultaneously releasing a predetermined number of objects (A,B) at the discharge station, each orientatable cell (6) including a seat (34) and a moveable clamp (27) for releasably retaining at least one object (A,B) in said seat, a roller (32) operatively coupled to said moveable clamp (27), and thrust means (50) acting on the rollers (32) associated with the orientable part of the cells at said discharge station (R).

7. The device as claimed in claim 6, wherein said objects are syringes having flanges thereon, and wherein the seat (34) and the movable clamp (27) on each cell releasably engage the flanges of said syringes.

* * * * *